United States Patent
Prescott et al.

(10) Patent No.: US 7,087,081 B2
(45) Date of Patent: Aug. 8, 2006

(54) STAPEDIAL PROSTHESIS AND METHOD OF IMPLANTING THE SAME

(75) Inventors: Anthony D. Prescott, Arlington, TN (US); Loren J. Bartels, Lutz, FL (US)

(73) Assignee: Clarity Corporation, Memphis, TN (US)

( * ) Notice: Subject to any disclaimer, the term of this patent is extended or adjusted under 35 U.S.C. 154(b) by 0 days.

(21) Appl. No.: 10/666,451

(22) Filed: Sep. 19, 2003

(65) Prior Publication Data

US 2005/0065603 A1    Mar. 24, 2005

(51) Int. Cl.
*A61F 2/18*    (2006.01)
(52) U.S. Cl. ...................................... 623/10
(58) Field of Classification Search ................ 623/10, 623/11; 600/25; 607/55, 137
See application file for complete search history.

(56) References Cited

U.S. PATENT DOCUMENTS

| | | | | |
|---|---|---|---|---|
| 2,792,958 A | * | 5/1957 | Beyer | 215/397 |
| 3,196,462 A | | 9/1961 | Robinson | 3/1 |
| 3,593,880 A | * | 7/1971 | Kulbacki | 220/697 |
| 3,711,869 A | | 1/1973 | Shea, Jr. | 3/1 |
| 3,838,468 A | | 10/1974 | Armstrong | 3/1 |
| 3,931,648 A | | 1/1976 | Shea, Jr. | 3/1.9 |
| 4,292,693 A | | 10/1981 | Shea et al. | 3/1.9 |
| 4,568,337 A | | 2/1986 | Treharne, III et al. | 604/247 |
| 4,606,329 A | | 8/1986 | Hough | 128/1 R |
| 4,612,915 A | | 9/1986 | Hough et al. | 128/1 R |
| 4,624,672 A | | 11/1986 | Lenkauskas | 623/10 |
| 4,655,776 A | | 4/1987 | Lesinski | 623/10 |
| 4,740,209 A | | 4/1988 | Gersdorff | 623/10 |
| 4,776,322 A | | 10/1988 | Hough et al. | 128/1.6 |
| 4,800,884 A | | 1/1989 | Heide et al. | 128/419 |
| 4,840,178 A | | 6/1989 | Heide et al. | 128/419 R |
| 4,957,507 A | | 9/1990 | Lenkauskas | 623/10 |
| 5,061,280 A | | 10/1991 | Prescott | 623/10 |
| 5,163,957 A | | 11/1992 | Sade et al. | 623/10 |
| 5,171,240 A | | 12/1992 | Hanwong | 606/1 |
| 5,220,918 A | | 6/1993 | Heide et al. | 128/420.6 |
| 5,306,299 A | | 4/1994 | Applebaum | 623/10 |
| 5,370,689 A | | 12/1994 | Causse | 623/10 |
| 5,433,749 A | | 7/1995 | Clifford et al. | 623/10 |
| 5,514,177 A | | 5/1996 | Kurz et al. | 623/10 |
| 5,522,896 A | | 6/1996 | Prescott | 623/16 |
| 5,531,787 A | | 7/1996 | Lesinski et al. | 623/10 |

(Continued)

OTHER PUBLICATIONS

"Titanium Grade 4", by Titanex.com, material specifications, downloaded at www.titane.ch/tigrtades/grade4.htm, on Aug. 17, 2003.

(Continued)

*Primary Examiner*—David J. Isabella
(74) *Attorney, Agent, or Firm*—Gordon & Jacobson, P.C.

(57) ABSTRACT

A stapedial prosthesis includes a body defining a bucket and a shaft, and a bail handle coupled to the bucket. The bucket is preferably adjustable in diameter to fit the incus lenticular process. The shaft preferably has a varying diameter, with a central portion of a smaller diameter than a distal portion which aids in depth perception during implantation and reduces mass to permit better sound energy transmission by the prosthesis. The bail handle is preferably spring-loaded and preferably constructed of titanium. The bail handle is preferably coupled to the body without crimping, twisting or welding and preferably biases the incus toward the bucket. A method of implanting a stapedial prosthesis is also provided.

20 Claims, 6 Drawing Sheets

U.S. PATENT DOCUMENTS

| | | | |
|---|---|---|---|
| 5,554,188 A | 9/1996 | Prescott | 623/10 |
| 5,728,157 A | 3/1998 | Prescott | 623/11 |
| 5,935,167 A | 8/1999 | a Wengen | 623/10 |
| 6,168,625 B1 | 1/2001 | Prescott | 623/10 |
| 6,197,060 B1 | 3/2001 | Knox | 623/10 |
| 6,203,571 B1 | 3/2001 | Magnan et al. | 623/10 |
| 6,436,139 B1 | 8/2002 | Shapiro et al. | 623/17.11 |
| 6,482,144 B1 | 11/2002 | Muller | 600/25 |
| 6,540,661 B1 | 4/2003 | Muller | 600/25 |
| 6,554,861 B1 | 4/2003 | Knox et al. | 623/10 |
| 6,726,719 B1 * | 4/2004 | Antonelli et al. | 623/11.11 |
| 2001/0027342 A1 | 10/2001 | Dormer | 623/10 |
| 2003/0018291 A1 | 1/2003 | Hill et al. | 604/8 |
| 2003/0130734 A1 | 7/2003 | Antonelli et al. | 623/10 |

OTHER PUBLICATIONS

"Titanium Metals" Unalloyed Titanium Commercially Pure (CP), RErjenterprises, down loaded at www.titanium-metals.com/titanium_cp.htm on Aug. 17, 2003.

"Titanium Grade 2", byTitanex.com, material specifications, down loaded at www.titane.ch/tigrtades/grade2.htm, on Aug. 17, 2003.

"Task Performance in Stapedotomy: Comparison Between Surgeons of Different Experience Levels" by Rothbaum et al., Otolaryngology—Head and Neck Surgery, Jan. 2003.

"Causse Piston". "De La Cruz Piston", "McGee Platinum/ Stainless Steel Piston Prostheses"& "Velegrakis Piston", product specifications, Gyrus ENT., 2003, downloaded at www.gyrus-ent.com on Aug. 17, 2003.

"The Lippy Stapes Prosthesis" product specification, The Lippy Group for Ear, Nose and Throat, downloaded at www.wog.com/lippy.html on Aug. 17, 2003.

"The Universal Titanium Prosthesis" product specification, Medtronic XOMED, 2001, Jacksonville, FL.

"Otosclerosis" by Katzenmeyer et al., Oct. 27, 1999.

"What is Titanium" etc., material specifications, Sibel, downloaded at www.sibelsa.be/titanium.html on Aug. 17, 2003.

* cited by examiner

STAPEDIAL PROSTHESIS AND METHOD OF IMPLANTING THE SAME

BACKGROUND

1. Field of Invention

The present invention relates to ossicular prostheses, more particularly to an improved stapedial prosthesis.

2. State of the Art

Medical Background: Stapes Diseases

Figure 1:
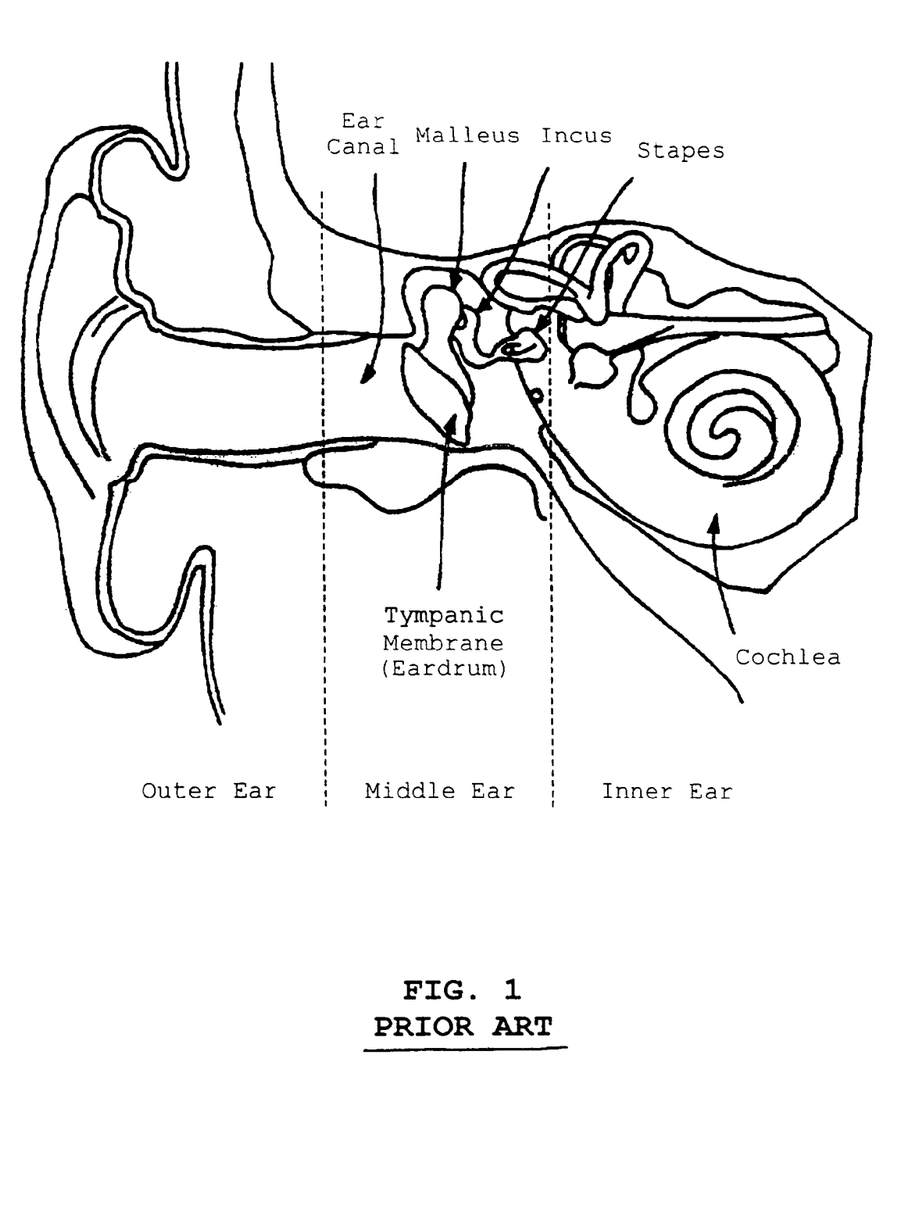
FIG. 1 is a cross-sectional profile of the human ear.
Figure 2:
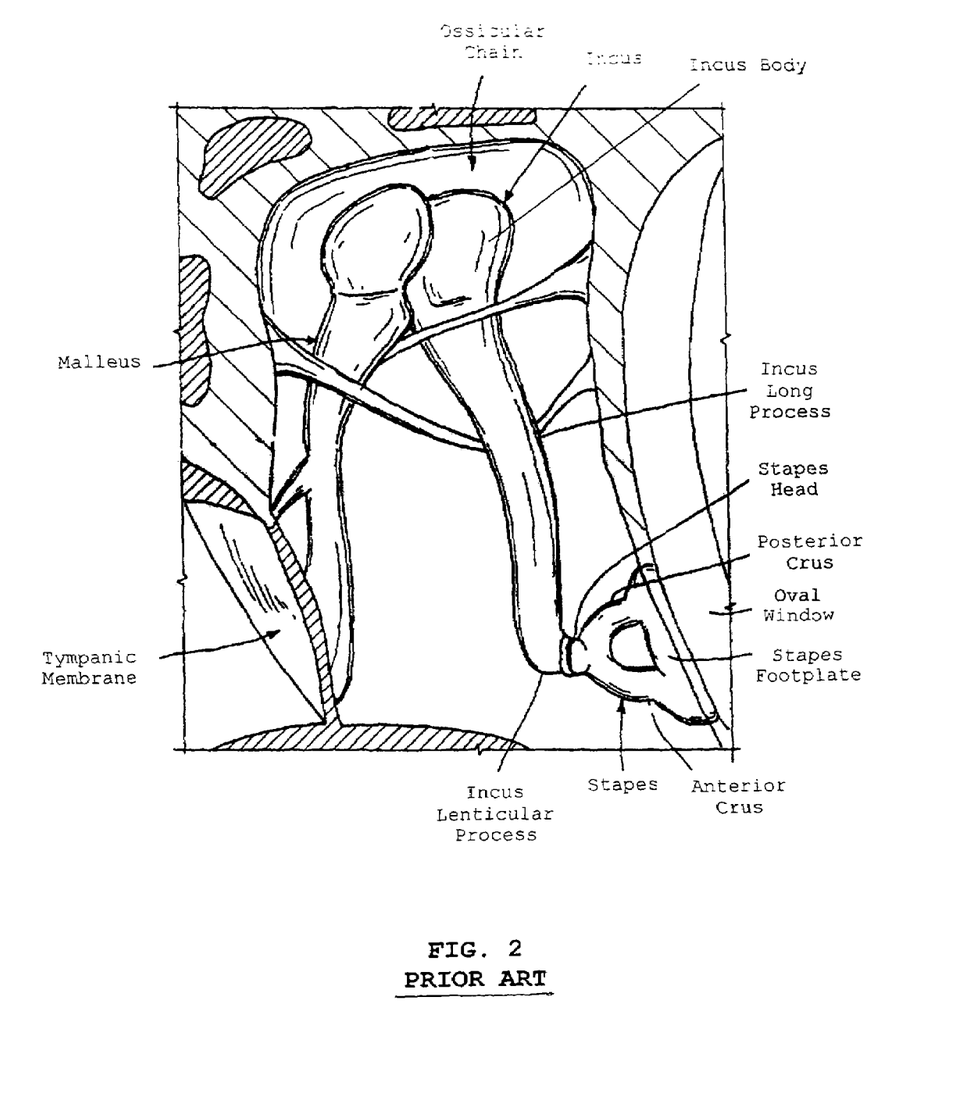
FIG. 2 is a cross-sectional profile of the human ear showing the ossicular chain.

Referring to prior art FIGS. 1 and 2, in a normal ear, sound energy, which consists of vibrations of air molecules, is directed by the auricle, or outer ear, through the ear canal to the tympanic membrane. Movements of the tympanic membrane are transferred to the ossicles, or the ossicular chain of the bones of the middle ear: malleus, incus and stapes. These movements eventually reach the inner ear labyrinth fluids via the stapes, which rests in a small groove, commonly called the oval window. The oval window is in intimate contact with the inner ear fluids. The movement of the inner ear fluids then stimulates the fine sensory organs of the inner ear, which in turn stimulate the auditory nerve, finally transferring the original sound energy to the brain.

Certain pathologies within the middle ear ossicular chain interrupt the transmission of sound energy and cause hearing loss. When this occurs, re-construction of the ossicular chain, using man-made prostheses, is often required. Three general conditions of discontinuity exist in which a prosthesis is appropriate. When the malleus, incus and stapes are absent, a Total Ossicular Replacement Prosthesis (or TORP) is used. When the stapes is absent but the malleus and incus are present, a Partial Ossicular Replacement Prosthesis (or PORP) is used. When the stapes footplate is fixed due to a condition referred to as otosclerosis, a stapes prosthesis is used.

Otosclerosis is one of the most common causes of progressive hearing loss in which there is an abnormal growth of bone in the ear. When otosclerosis is present there is an abnormal, microscopic growth of bone in the walls of the middle ear. This abnormal growth impedes the conduction of sound energy from the tympanic membrane to the inner ear. In particular, otosclerosis affects the stapes bone by causing it to become frozen in place or "fixed." Normally the stapes vibrates freely to allow the transmission of sound energy into the inner ear. When it becomes fixed to the surrounding bone, it prevents sound waves from reaching the inner ear fluids, and thus hearing is impaired.

When the amount of otosclerosis at this location is significant, as determined by careful hearing tests, surgery has been found to be the most effective method of improving hearing loss caused by this condition. This surgery is termed a stapedectomy and serves to restore continuity between the incus and inner ear fluids. A stapedectomy is sometimes performed in patients who have a congenital abnormality of the stapes or have sustained a fracture of the stapes from traumatic incident. However, the most common indication for a stapedectomy is otosclerosis.

Medical Background: Stapedectomy Surgery Technique

Surgical treatment for otosclerosis has been available for about 45 years. The first operation for this disease was the fenestration procedure, which required mastoid surgery and an artificial opening in another part of the inner ear. The attention of surgeons became focused on the diseased stapes itself and the stapes mobilization procedure was developed. With the improvement in surgical techniques, the treatment of choice became stapedectomy. This procedure was first performed in 1956 and has remained the mainstay of treatment for otosclerosis.

The objectives of stapedectomy are: (1) to open the oval window for sound entry into the inner ear labyrinth; (2) to reconstruct a conductive bridge between the incus and the labyrinth; and (3) to accomplish these goals as efficiently and physiologically compatible as possible for long-term hearing without complication. To accomplish these objectives the stapedectomy is performed through an incision in the ear canal under local or general anesthesia. A flap consisting of canal skin and tympanic membrane is elevated and the posterior superior bony external auditory canal wall is removed, usually by a drill, to expose the malleus, incus, stapes and chorda tympani (facial nerve). The ossicles are inspected and palpated to establish the precise diagnosis of the conductive hearing loss; that is, the fixation of the stapes and mobility of the malleus and incus are confirmed. The distance between the undersurface of the incus and the stapes footplate is then measured to determine the prosthesis length.

With care taken to preserve the chorda tympani, the synovial joint between the lenticular process of the incus and the head of the stapes is separated (incudostapedial joint). The stapes tendon and one crus (leg) of the stapes is then severed. The arch of the stapes may then be removed by fracturing the other crus while allowing the stapes footplate to remain in the oval window. An opening is created in the footplate to allow entrance for a stapedial prosthesis. In some cases, the footplate is removed and a vein is grafted to the internal wall of the tympanum to cover the opening and to support the stapes prosthesis. After the opening is made in the footplate, or tissue is placed over the opening made to the inner ear after removing the footplate, one end of a stapedial prosthesis of proper length is posted in the opening while the other end is attached to the incus. The incus is gently palpated to observe the motion of the stapedial prosthesis. A piece of fat or tissue is applied (obtained, as one example, from a small incision behind the ear lobe) in order to seal any hole in the oval window. Finally, the eardrum is folded back into its normal position.

Medical Background: Prior Art Prostheses

A critical part of the stapedectomy procedure is attaching the prosthesis around the lenticular process of the incus due to its miniature size, typically about 3.5 mm to 6 mm long and 0.4 mm to 0.8 mm diameter, and its delicate nature. There have been several devices proposed for the stapedial prosthesis. One class includes those that use a crimping technique. For instance, in U.S. Pat. No. 5,370,689 to Causse, one end of the prosthesis, fabricated of PTFE, is posted in an opening drilled in the exposed footplate, and a split eyelet at the other end must be crimped around the incus. In U.S. Pat. No. 3,711,869 to Shea Jr. one end of the prosthesis is placed on a vein graft invaginated into the oval window, and a split eyelet at the other end must be forced open by elastic deformation to fit onto the incus. Elastic recovery capacity of the eyelet causes it to restore to its original form in about 20 minutes and grip the incus firmly. U.S. Pat. No. 3,838,468 to Armstrong discloses a stapedial prosthesis for use in cases where the footplate is also removed. A piston is fixed at one end to a vein graft for covering the oval window. A wire of stainless steel, platinum, gold, or like biocompatible material shaped like a shepherd's crook extending from the other end, is crimped about the lenticular process of the incus.

Figure 3:
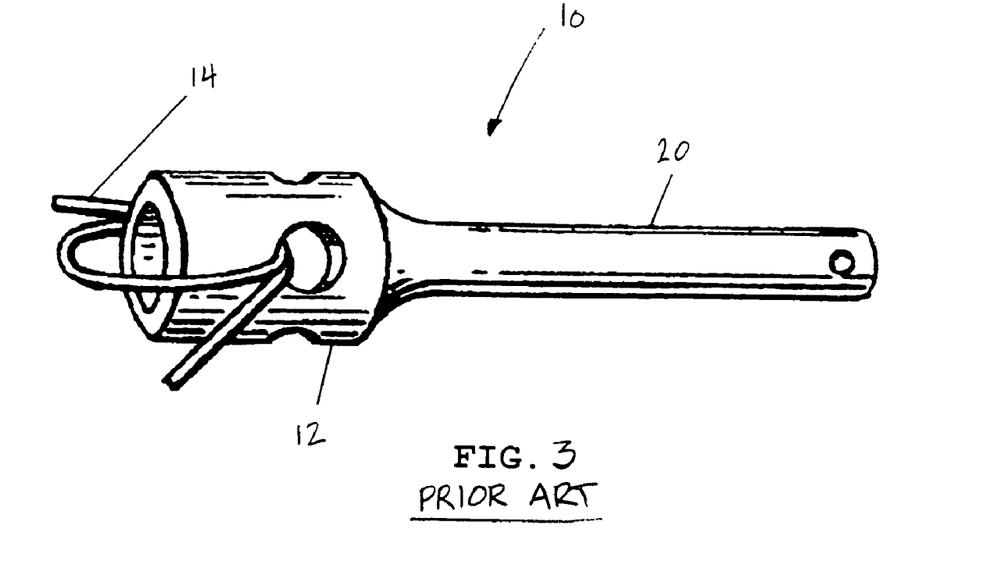
FIG. 3 is a perspective view of a prior art bucket-handle stapedial prosthesis.
Figure 4:
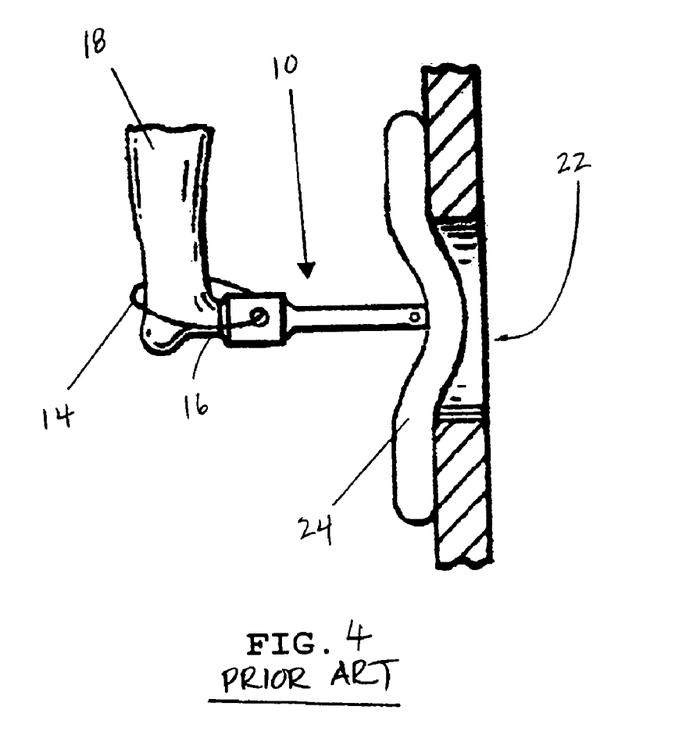
FIG. 4 is a side elevation view of the prior art stapedial prosthesis of FIG. 3, shown implanted between the incus and the oval window.

Another type of prosthesis in use is the "bucket-handle prosthesis," which in comparison to the traditional crimped stapes prosthesis discussed above, is reportedly easier to insert (as discussed by Rothbaum, et. al in "Task performance in stapedotomy: Comparison between surgeons of different experience levels," *Otolaryngol Head Neck Surg.* 128:71–7 (2003)). Referring to prior art FIGS. 3 and 4, U.S. Pat. No. 3,196,462 to Robinson discloses one type of bucket-handle device 10, also termed the bucket-and-bail device, which includes a bucket 12 (also termed a well or a socket), a wire bail 14 (handle) at one end for receiving and securing a portion of the disarticulated lenticular process 16 of the incus 18, and a cylindrical shaft portion 20 (or stem or rod) at the other end for engaging the oval window 22, or tissue 24 (e.g., a vein graft or fat tissue) that is placed over the opening made to the inner ear after removing the footplate. The bail 14 is oriented by the surgeon so that its axis of pivotal rotation generally is horizontal. With the prosthesis 10 in that configuration, the incus lenticular process 16 is positioned in the bucket 12 and the bail 14 is rotated in an upward arc about a fulcrum point on the bucket, past the horizontal, until the bail contacts the long process of the incus 18. In this particular device, only the frictional engagement of the bail 14 against the incus 18 holds the bail in place. If the bail should rotate downwardly, out of range of contact with the incus, the prosthesis may become dislodged and extrusion may result. In contrast, with a crimpable wire-crook prosthesis, a short term risk is that the prosthesis will fracture the incus. Additionally, a loose fitting crimpable prosthesis may erode or wear away the incus from irregular loose vibration. Thus, the challenge of stapedial prostheses, whether a bucket-and-bail type or a crimpable type is to secure the prosthesis sufficiently well to the incus to avoid its failing out of position while being careful not to have a connection to the incus that allows the incus to erode or to fracture.

U.S. Pat. No. 4,292,693 to Shea et. al discloses one means for overcoming the bail securement problem. Referring to prior art FIGS. 5 and 6, the stapedial prosthesis 40 of Shea et al. provides a pair of cam surfaces 42 oppositely mounted on the bucket portion 44 which permits overcenter pivotal movement of the bail 46 in one direction and thereafter prevents overcenter pivotal movement of the bail in the opposite direction. Each of the cam surfaces 42 tapers outwardly from the surface of the bucket portion 44 in the direction the overcenter pivotal movement of the bail 46 is permitted, and terminates in an inwardly extending shoulder portion 48 which engages the bail 46 to prevent the overcenter pivotal movement thereof in the opposite direction.

Figure 5:
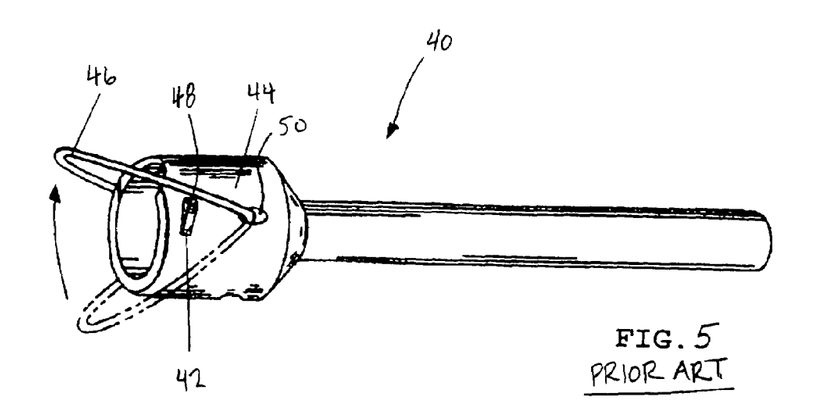
FIG. 5 is a perspective view of another prior art bucket-handle stapedial prosthesis.
Figure 6:
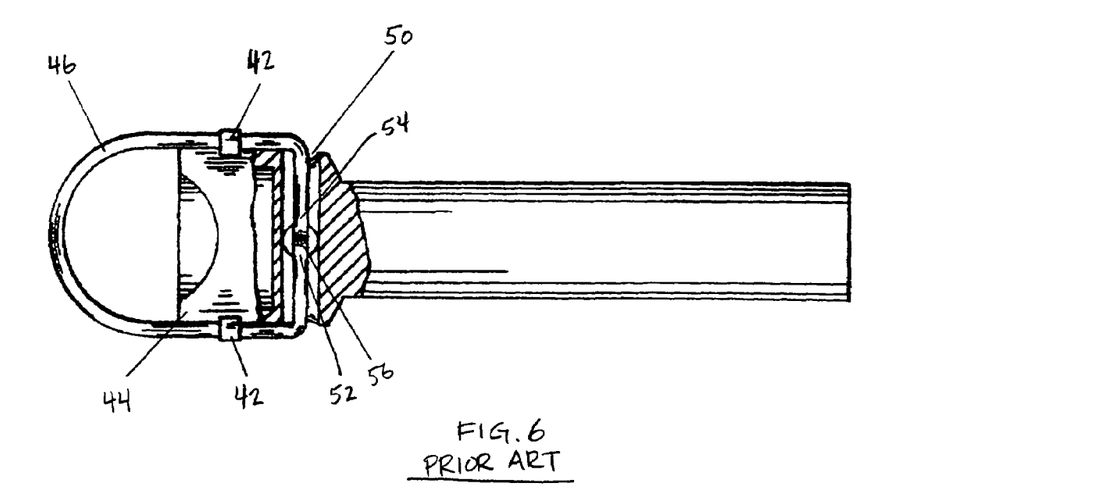
FIG. 6 is a cross-sectional profile of the prior art stapedial prosthesis of FIG. 5, showing the weld joint of the wire bail.

Currently, these bail handles are constructed from stainless steel. Current attachment methods of the bail handle to the bucket in bail-and-bucket device require that the bucket handle protrude into the bucket of the prosthesis, thus disturbing the incus process as it lies in the bucket, which further creates problems in measuring the prosthesis bucket for a correct fit. During the manufacturing process, a through-hole 50 is first made completely through the bucket body 44. The bail 46 is then formed into a generally elongated D-shaped configuration with ends turned inwardly at right angles. The bail 46 is preferably formed of a single strand of stainless steel wire with its ends 52, 54 joined in abutting relationship as by a weld 56, twisting or crimping. The stainless steel material of the bail 46 is such that one end may be deformed and inserted completely through the hole 50 so that the weld 56 may be made. Thereafter, the weld 56 is pulled into the through-hole 50 until it is approximately centered and the deformed portion resumes its original shape. This securement method results in a variability of size and maneuverability in the bail handle, which further complicates the surgical insertion of the device.

It is readily apparent that great care and skill are required to secure these and similar prostheses to the lenticular process of the incus. The minute size of the prostheses also makes them extremely difficult to manipulate into proper position for tightening around the incus, even with state-of-the-art microsurgical instrumentation. This is made more difficult as during the stapedectomy surgery, the view at the prosthesis insertion site is restricted.

As mentioned above, measurement and selection of the prosthesis, which is affected by current manufacturing processes, is critical for proper functionality. Once in place, if the prosthesis is not tightened sufficiently about the incus, fluctuating hearing loss, dizziness, or extrusion of the prosthesis may occur. If it is too tight, necrosis of the incus may occur. In either case, the securement method in itself may cause trauma to the delicate middle ear structures, including fracture or subluxation (dislocation) of the incus.

Therefore, from the above, it can be appreciated that there is a need for an improved bucket-handle prosthesis, particularly with respect to manufacturing repeatability of the bail handle and easier and more proficient attachment to the incus process.

SUMMARY OF THE INVENTION

It is therefore an object of the invention to provide an improved bucket-handle stapedial prosthesis.

It is another object of the invention to provide a stapedial prosthesis which facilitates manufacture, assembly and surgical implantation.

It is also an object of the invention to provide a visual cue for the surgeon that aids in depth perception while operating in the middle ear area.

It is an additional object of the invention to provide a stapedial prosthesis that better conforms to a patient's anatomy.

It is a further object of the invention to provide a stapedial prosthesis that is adaptable in size for the incus.

It is yet another object of the invention to provide a stapedial prosthesis that provides better transmission of sound energy, and thus better hearing results.

It is yet an additional object of the invention to provide a stapedial prosthesis that does not cause artifacts on MRI images.

In accord with these objects, a stapedial prosthesis is provided and includes a bucket body, a bail handle, and a shaft. In accord with one preferred aspect of the invention, the bucket body preferably includes a plurality of slots positioned in the bucket wall which allow selected segments of the bucket wall to bend inwardly or outwardly. When these wall segments are manipulated by the surgeon, the bucket can adapt to a variety of incus process diameters.

In accord with a second preferred aspect of the invention, the prosthesis overcomes certain problems in the prior art by constructing the bail handle from a resilient material, such as titanium. By using the spring-like tension of titanium, the bail handle is secured in two holes within the wall of bucket body in such a way that allows complete freedom and unobstruction to the incus process as it lies in the bucket. The spring tension of the bail handle causes the handle to remain affixed to the bucket without welding, twisting or crimping, and the handle does not extend all the way through the body as in prior art devices. Since there is no welding, twisting or crimping, there is a more uniform fit and movement of the bail handle when attached to the bucket, thus aiding further in the installation of the prosthesis. Furthermore, the handle, once manipulated by the surgeon, remains in a fixed relation relative to the bucket. Additionally, the use of titanium provides less imaging artifact in magnetic resonance imaging situations as titanium is a more MRI transparent material than stainless steel.

In accord with a third preferred aspect of the invention, visualization of the prosthesis during implantation is aided by providing a shaft portion of the device with a central portion having a relative smaller diameter than a distal end portion which attaches to or adjacent the anatomical oval window. This change in dimension provides a visual cue for the surgeon as the surgeon places the prosthesis into the opening made in the oval window. The smaller diameter central portion of the shaft also helps to reduce the mass of the device thus aiding in the sound energy transmission from the tympanic membrane to the inner ear.

Additional objects and advantages of the invention will become apparent to those skilled in the art upon reference to the detailed description taken in conjunction with the provided figures.

BRIEF DESCRIPTION OF THE DRAWINGS

Prior art

Prior art

Prior art

Prior art

Prior art

Prior art

DETAILED DESCRIPTION OF THE PREFERRED EMBODIMENTS

Referring to FIGS. 7 through 10, a preferred embodiment of a stapedial prosthesis 100 includes a body 102 and a bail handle 104. The body 102 is preferably constructed from commercially pure Grade 2 titanium, and is further defined by a closed-bottom bowl shaped cavity, termed the bucket 106 (or well), which tapers down to a shaft 108 (also termed a stem or a rod). The bucket 106 of the body 102 is sized to accept the long process and lenticular process of the incus. The body 102 of the prosthesis 100 preferably defines four holes 110, 112, 114, 116, each designed for a specific purpose as now described. The two diametrically-opposed holes 110, 112 near the bottom of the bucket 106 are receptacles (bail insert openings) for receiving ends 118, 120 of the bail handle 104, described below. The hole 114 located at the rear of the bucket 106 near the rim 142 is intended for positioning the prosthesis 100. That is, a surgeon can insert a pick 200 and turn the prosthesis 100 to achieve an optimum fit for each patient, as described in more detail below with respect to FIG. 11. The hole 116 near the distal end of the shaft 108 is optional, and where provided allows for tissue in-growth and further stabilization of the device, as the distal end of the shaft end engages the oval window, or graft tissue that is placed over the fenestration made to the inner ear after removing the anatomical footplate, as described in detail below.

Figure 10:
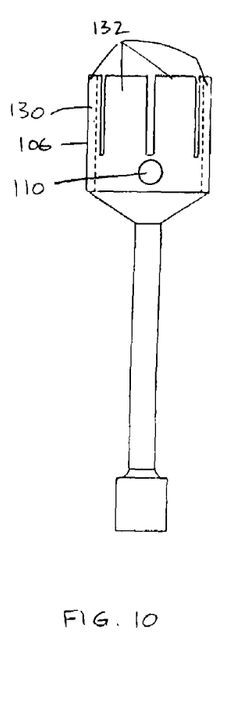
FIG. 10 is a right side elevation view of the stapedial prosthesis of FIG. 7.

According to one preferred aspect of the prosthesis 100, the diameter of the bucket 106 is adjustable. A preferred mechanism for adjusting the diameter includes a plurality of slots 128 provided in the wall 130 of the bucket 106 (four slots being shown, although more or fewer could be used) which define individual wall segments 132 (FIG. 10). Each slot 128 is preferably about 0.1-mm wide, and defines an arc about the circumference of the bucket 106 which is substantially smaller than that traversed by each wall segment 132, e.g., by a factor of four or more. The slots 128 permit the segments 132 of the bucket wall 130 to be bent inwardly or outwardly. When the wall segments 132 are manipulated by the surgeon, the bucket can adapt to a variety of incus process diameters. Note that the slots 128 preferably extend down the side of the bucket 106 until just above the bail insert openings 110, 112, thus not affecting the bail-to-bucket connection, described below.

Figure 9:
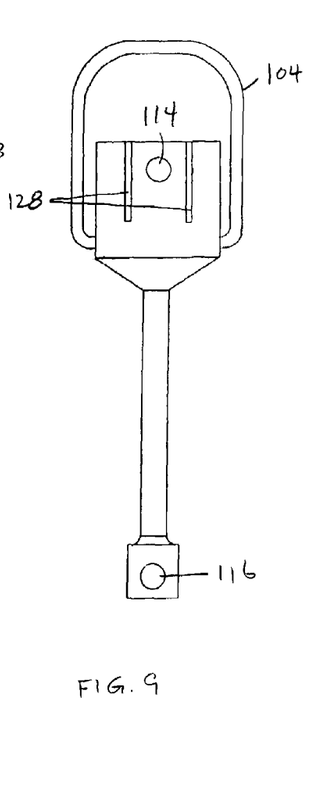
FIG. 9 is a rear elevation of the stapedial prosthesis of FIG. 7.

The bucket 106 optionally has an incus notch 140 in the rim 142 of the bucket wall 130. A prosthesis with an incus notch 140 in the bucket 106 is generally selected by the surgeon when a determination is made that the incus is too eroded or too short for a closed (non-notched) bucket. As such, alternatively, a closed bucket can be provided to the prosthesis for use with an incus having good form. In such an embodiment, the front and rear views of the bucket 106 would generally be as shown in FIG. 9, with manipulation hole 114 optionally not being provided at the front of the bucket.

According to another preferred aspect of the prosthesis 100, the bail handle 104 is a generally U-shaped or smoothly-arced structure. In addition, the handle is preferably constructed from titanium, and more preferably 0.125-mm (0.005") diameter commercially-pure Grade 4 titanium. The handle 104 has end portions 118, 120 which are inwardly directed toward each other and define a space therebetween that is smaller than the outer diameter of the bucket 106 at the bail insert openings 110, 112.

The handle 104 is designed to be freely manipulated by the surgeon relative to the bucket 106 (rotating about the openings 110, 112) so that it can be flipped up and over the incus once the incus lenticular process has been placed in the bucket 106 of the prosthesis 100. The handle 104 acts as a means for stabilizing the prosthesis relative to the incus process by holding the incus in place, and further prevents the prosthesis from slipping off of the incus. The properties of titanium, as the preferred material for the handle, contribute in several areas with respect to the prosthesis 100. Since titanium has better spring-like mechanical properties than stainless steel, this characteristic can be used to hold the handle 104 to the bucket 106 of the prosthesis, e.g., the spring-like tension forces the ends 118, 120 of the handle 104 into the bail insert openings 110, 112, thus holding the handle 104 to the bucket 106 without the need for welding, twisting or crimping. The ends 118, 120 of the bail handle 104 are not coupled to each other, do not contact each other, and do not pass each other within the bucket 106. And once manipulated by the surgeon, the bail handle 104 under tension remains in a fixed relationship relative to the bucket 106 without concern of unintended movement which may otherwise result in undesirable loosening of the incus relative to the prosthesis 100.

With respect to manufacturing and assembly advantages, because the handle 104 is formed prior to assembly, and considering the handle material is preferably titanium, the handle has a relatively low mass and presents a more uniform, repeatable shape. During the assembly process, the ends 118, 120 of the handle 104 are slightly spread apart, manipulated about the bucket 106 and then released into the bail insert openings 110, 112 of the bucket 106 of the prosthesis, a much simpler method than current approaches. Due to this simplified assembly technique, manufactured units are more uniform. Furthermore, the bail handle 104 does not protrude into the bucket 106, and thus the cavity of the bucket 106 remains open permitting a more complete fit of the incus process within the bucket.

Figure 7:
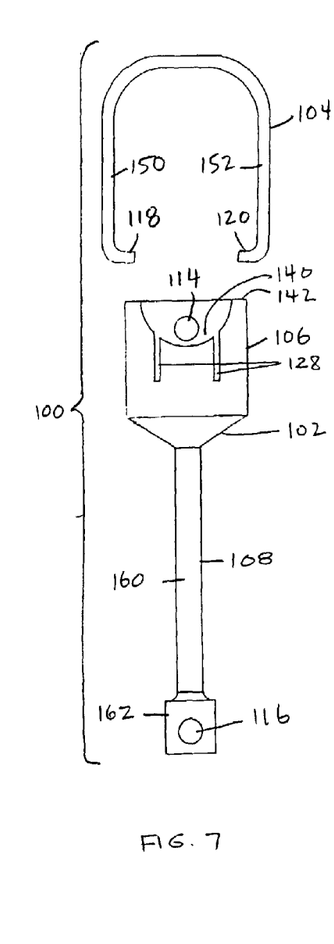
FIG. 7 is an exploded view of a bucket-handle stapedial prosthesis according to the present invention.
Figure 8:
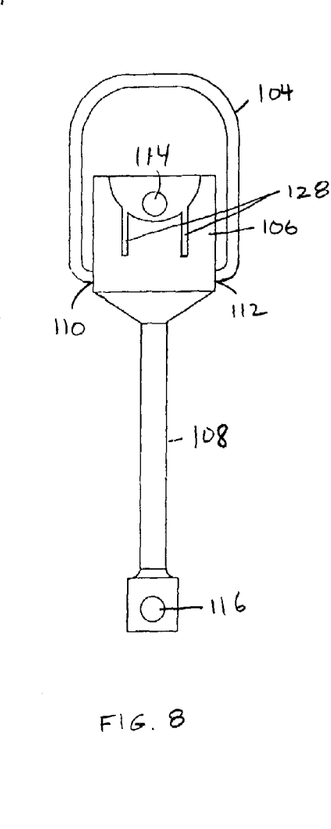
FIG. 8 is a front elevation view of the stapedial prosthesis of FIG. 7.

Referring specifically to FIG. 7, according to another preferred aspect of the prosthesis, the shaft 108 of the stapedial prosthesis 100 has a central section 160 and a distal section 162 of different diameters. The bucket 106 tapers down to the central section 160 of the shaft 108 to a diameter of approximately 0.3-mm. The shaft 108 continues at this diameter until reaching the distal section 162 where it enlarges in diameter, preferably to approximately 0.4-mm to 0.8-mm. This varying diameter provides at least two advantages. First, the mass of the prosthesis 100 is reduced, which in turn aids in the conduction of sound, and thus the patient's hearing. Second, a visual cue is provided to the surgeon of the location of the distal section 162 of the prosthesis within the middle ear area.

Figure 11:
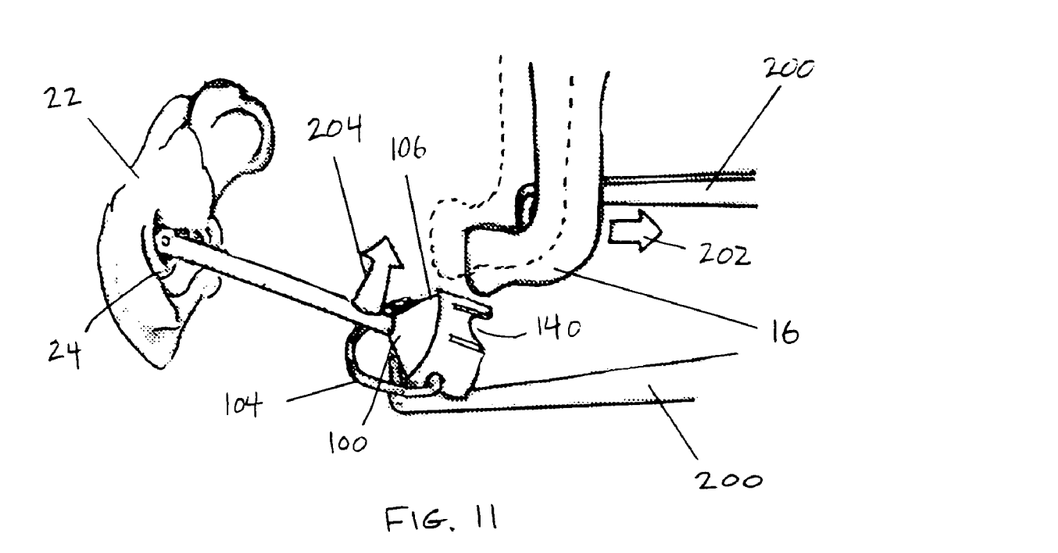
FIG. 11 is a perspective view of a first portion of the stapedial prosthesis implantation procedure.
Figure 12:
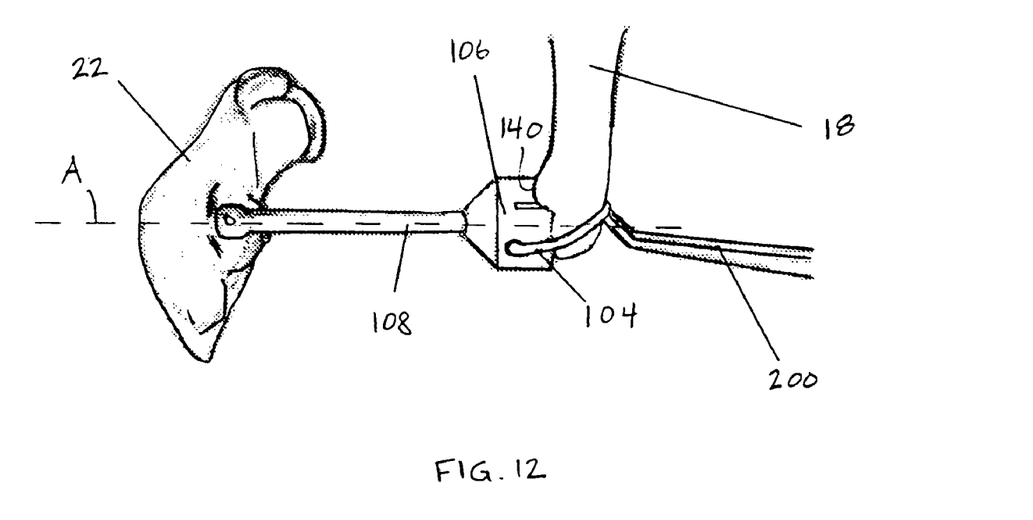
FIG. 12 is a perspective view of a second portion of the stapedial prosthesis implantation procedure.

Referring now to FIGS. 11 and 12, the implantation of the prosthesis 100 will now be described, wherein the prosthesis is provided with the incus notch 140. Implantation using a closed bucket (non-notched) design proceeds in a similar manner.

Referring specifically to FIG. 11, after the surgeon removes the stapes and performs the necessary steps preparatory to implantation of the stapedial prosthesis of the present invention, e.g., creating a stapedotomy opening in the footplate to allow entrance for the stapedial prosthesis, or covering the oval window 22 with a tissue graft 24 of the surgeon's choice, the prosthesis 100 is inserted into position using forceps. In so doing, the distal section 162 of the prosthesis is placed against the graft tissue 24. The prosthesis can be manipulated into a desired orientation by engaging the upper opening 114 of the prosthesis 100 with a right angle pick tool 200 and manipulating the prosthesis therewith. In proper orientation, the incus notch 140 will be located at the top of the lenticular process 16 of the incus 18, with a portion of the lenticular process inserted into the incus notch 140 of the bucket 106. During the initial step of the insertion procedure, the bail handle 104 is rotated to the side of the bucket 106 having the upper opening 114 for the positioning tool (i.e., opposite the notch 140). The surgeon then gently moves the incus process (in the direction of arrow 202), rotates the prosthesis (in the direction of arrow 204), and sets the lenticular process 16 into the bucket 106.

Where the bucket wall 130 is segmented, the surgeon has two options for adapting the size of the bucket 106 to the size of the incus process 16. In a first approach, after placing the incus lenticular process 16 into the bucket 106, the surgeon bends one or more of the wall segments 132 (FIG. 10) until just touching the process 16, thus gripping the incus 18. At this point the surgeon rotates the bail handle 104 to further hold the incus relative to the prosthesis, preferably as follows. Referring to FIG. 12, the surgeon rotates and pulls the bail handle 104 upward and outward so that the bail handle 104 passes through a plane containing both the bail handle and the longitudinal axis A of the prosthesis. The surgeon continues the upward and outward rotation of the bail handle 104 until it is in proper position about the long process of the incus 18. As the surgeon releases the spring-loaded bail 104, the tension in the bail handle 104 may aid in holding the incus process 16 within the bucket 106.

In a second approach, the surgeon would place the incus lenticular process 16 into the bucket 106, rotate the bail 104 as described above, then bend one or more wall segments 132 (FIG. 10) until just touching the process, thus gripping the incus 18 further.

As yet another alternative, the wall segments 132 may be left in their manufactured configuration, and the force of the bail handle 104 alone is used to hold the incus process 16 relative to the prosthesis 100.

With respect to post-operative considerations, the preferably all-titanium prosthesis has excellent bio-compatibility and, due to its non-magnetic nature, has little effect on magnetic resonance imaging (e.g., very low MRI image artifacts).

The device may be constructed in a range of dimensions with respect to bucket diameters, shaft diameters, and lengths. In this manner, a device can be selected by the surgeon that corresponds to the anatomical features of a patient. Exemplar dimensions follow. The overall length of the body 102 (bucket 106 and shaft 108) is 3.5-mm to 9.0-mm. The bucket 106 has a length of 0.8-mm to 1.3-mm, a diameter of 0.85-mm to 1.5-mm, and a wall thickness of 0.1525-mm. One preferred inner diameter of the bucket 106 is 0.965-mm and one preferred outer diameter of the bucket is 1.27-mm. Each of the four holes 110, 112, 114, 116 has a diameter of approximately 0.150-mm. The bail handle 104 has a length of 2.13-mm, a width (across parallel shaft portions 150, 152 of FIG. 7) of 1.49-mm, and a cross-sectional diameter of 0.125-mm. The shaft 108 has a length of 2.7-mm to 7.7-mm, and a diameter of 0.4-mm to 0.8-mm. Where the shaft has the preferred varying diameter, the central section 160 preferably has a length of 2.4-mm to 6.7-mm and a diameter of 0.3-mm, and the distal section preferably has a length of 0.3-mm to 1.0-mm and a diameter of 0.4-mm to 0.8-mm.

There have been described and illustrated herein embodiments of a stapedial prosthesis and methods of implantation of the same. While particular embodiments of the invention have been described, it is not intended that the invention be limited thereto, as it is intended that the invention be as broad in scope as the art will allow and that the specification be read likewise. Thus, while several preferred aspects of the invention have been described with respect to the figures, it is intended that each of the preferred aspect and other aspects of the invention may be implemented independently or in combination with one or more other aspects of the invention. That is, each of the segmented bucket, the spring-tensioned bail handle, and the shaft with reduced diameter central portion may be implemented in an otherwise conventional stapedial prosthesis with or without the other preferred aspects. In addition, while particular exemplar dimensions have been disclosed, it is understood that other dimensions can be provided to the elements of the prosthesis provided such dimensions allow the prosthesis to be used as a stapedial prosthesis. Also, while titanium, and more particularly preferred specific grades of titanium, have been disclosed, it is appreciated that the preferred aspects of the invention may be implemented in materials other than titanium. It will therefore be appreciated by those skilled in the art that yet other modifications could be made to the provided invention without deviating from its spirit and scope as claimed.

What is claimed is:

1. A stapedial prosthesis sized to be implanted as a replacement for the stapes between the incus and the oval window of the middle ear, comprising:
    a) a body defining a bucket and a shaft, said bucket sized to at least partially receive a portion of an incus and having a wall with a plurality of slots defining wall segments, a portion of said bucket being adjustable in diameter by manipulation of said wall segments and retaining said adjusted diameter after a force causing said adjusted diameter is removed, and said shaft having a length sufficient to extend from the incus to the oval window, said shaft having a central portion and first and second end portions, said central portion having a diameter of approximately 0.3-mm, said first end portion having a diameter of approximately 0.4-mm to 0.8-mm, and said second end portion being coupled to said bucket; and
    b) a bail handle coupled to said bucket.

2. A stapedial prosthesis according to claim 1, wherein:
said slots arc approximately 0.1-mm wide.

3. A stapedial prosthesis according to claim 2, wherein:
said slots define arcs about a circumference of the bucket which are substantially smaller than arcs traversed by the wall segments defined by the slots.

4. A stapedial prosthesis according to claim 2, wherein:
said arcs defined by said slots are smaller than said arcs defined by said wall segments by a factor of at least four.

5. A stapedial prosthesis according to claim 1, wherein:
said bucket has a closed bottom portion.

6. A method of implanting a stapedial prosthesis between the incus and oval window of the middle ear, comprising:
    a) providing a stapedial prosthesis including a bucket with a plurality of wall segments, a shaft fixed to the bucket, and a spring-loaded bail handle movably coupled to the bucket, the bail handle oriented so as to provide clear entry to the bucket;
    b) positioning a portion of the incus into the bucket;
    c) moving the bail handle until the bail handle contacts the incus; and
    d) bending one or more segments of the wall of the bucket to adjust a diameter of said bucket to the incus, said bucket retaining said adjusted diameter after said bending force is removed.

7. A method according to claim 6, wherein:
said bending includes bending one or more segments until at least one of the segments contacts the incus.

8. A method according to claim 6, wherein:
said bending occurs before said moving.

9. A method according to claim 6, wherein:
said bending occurs after said moving.

10. A method according to claim 6, wherein:
said moving the bail handle includes rotating the bail handle.

11. A method according to claim 10, wherein:
said moving the bail handle includes pulling the bail handle over a portion of the incus.

12. A method according to claim 11, wherein:
said moving the bail handle includes causing the bail handle to pass through a plane containing both the bail handle and a longitudinal axis of the bucket and the shaft.

13. A method according to claim 6, wherein:
said moving the bail handle includes biasing the incus relative to the bucket with the spring-loaded bail handle.

14. A method according to claim 6, wherein:
after said moving, the bail handle is substantially fixed relative to the bucket via the spring-load on the bail handle.

15. A method according to claim 6, wherein:
said providing includes providing a stapedial prosthesis with a titanium bail handle.

16. A stapedial prosthesis according to claim 1, wherein:
said shaft is stepped in diameter.

17. A stapedial prosthesis according to claim 1, wherein:
said shaft is made of a metal or metal alloy, and said first end portion defines holes sized for tissue ingrowth.

18. A stapedial prosthesis according to claim 1, wherein:
said first end portion has a length not exceeding 1-mm.

19. A stapedial prosthesis according to claim 1, wherein:
said first end portion has a length greater than 0.3-mm.

20. A stapedial prosthesis according to claim 1, wherein:
said central portion has a length at least approximately 2.4 times a length of said first end.

* * * * *